United States Patent
Zhang et al.

(10) Patent No.: US 6,232,111 B1
(45) Date of Patent: *May 15, 2001

(54) METHOD FOR IMPROVING CULTURE MEDIUM FOR RECOMBINANT YEAST

(75) Inventors: Jinyou Zhang, Edison; Randolph L. Greasham, Mountainside, both of NJ (US)

(73) Assignee: Merck & Co., Inc., Rahway, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/831,288

(22) Filed: Mar. 31, 1997

Related U.S. Application Data

(60) Provisional application No. 60/015,250, filed on Apr. 10, 1996.

(51) Int. Cl.[7] .................................................. C12N 1/18
(52) U.S. Cl. .................. 435/254.21; 435/254.2; 435/254.22; 435/254.23
(58) Field of Search ........................... 435/254.2, 254.21, 435/254.22, 254.23

(56) References Cited

U.S. PATENT DOCUMENTS 4,863,864   9/1989   Ashikari et al. ..................... 435/205

FOREIGN PATENT DOCUMENTS

95/01422 * 1/1995 (EP).

OTHER PUBLICATIONS

Stewart et al., 1950, J. Am Chem. Sco., vol. 72, pp. 2059–2061.*

Cook, A.H., "The Chemistry and Biology of yeasts", 1958, Academic Press, pp. 277, 391–392 and 508.*

Carty et al, J. Jud. Microbiol., (1987) 2: 117–121.*

Dey, et al., "The Glycosylation of Phosphoglucomutase Is Modulated by Carbon Source and Heat Shock .. .", The Journal of Biol. Chem., vol. 269, No. 43, pp. 27143–27148, 1994.

MacKenzie, et al., "Water Stress Hypersensitivity of Yeasts: Protective Rile of Treholose in *Saccharomyces Cerevisiae*", J. of General Microbiology, vol. 134, pp. 1661–1666, 1988.

Hottiger, et al., "The 70–kilodalton heat–shock proteins of the SSA subfamily negatively modulate heat–shock–induced . . .", Eur. J. Biochem., vol. 210, pp. 125–132, 1992.

Farris, et al., "A Genetically Improved Wine Yeast", Biotechnology Letters, vol. 14, No. 3, pp. 219–222, Mar. 1992.

* cited by examiner

*Primary Examiner*—Irene Marx
(74) *Attorney, Agent, or Firm*—Michael D. Yablonsky; Jack L. Tribble

(57) ABSTRACT

Yields in yeast recombinant expression systems are improved by identifying bad lots and supplementing them with the appropriate combination of adenine, trehalose and/or lactate.

6 Claims, No Drawings

METHOD FOR IMPROVING CULTURE MEDIUM FOR RECOMBINANT YEAST

This application claims the benefit of U.S. Provisional Application No. 60/015,250, Apr. 10, 1996.

CROSS-REFERENCE TO RELATED APPLICATIONS

This is related to U.S. Ser. No. 086,216, filed Jul. 1, 1993, now published as WO 95/01422.

STATEMENT REGARDING FEDERALLY-SPONSORED R&D

Not applicable.

REFERENCE TO MICROFICHE APPENDIX

Not applicable.

FIELD OF THE INVENTION

Not applicable.

BACKGROUND OF THE INVENTION

Production of compounds of pharmaceutical significance by cultivation of recombinant yeasts is an expanding field of science and commerce. Purified recombinant hepatitis B surface antigen (HBsAg) is used as a vaccine for hepatitis B viral disease and is a well-known example of a pharmaceutically-significant recombinant protein.

Recombinant HBsAg is produced by cultivation of yeast cells in complex or chemically-defined (synthetic) culture media. Generally, complex media contain crude sources of nitrogen such as yeast extract and peptones. Although high yields of cells and crude HBsAg are achieved in these complex culture media, overall performance is frequently variable, and sometimes unacceptably inconsistent. Inconsistencies in fermentation performance adversely affect downstream purification steps and may also increase costs for the purified product.

Regulated expression systems are commonly used for the production of recombinant proteins. One type of regulated system provides tight nutritional control of the production of heterologous protein. This type of system maximizes biomass production and product stability while minimizing the adverse effects of heterologous protein expression on the host cell, e.g., Zabriskie et al., *Enzyme Microbial Technol.* 8:706–717 (1986).

For convenience, applicants employ a recombinant *S. cerevisiae* strain for the production of Recombivax HB® (a trademark of Merck & Co. Inc.), which strain harbors a plasmid composed of the coding sequence for HBsAg linked to the glyceraldehyde-3-phosphate dehydrogenase (GAP) promoter, as well as an origin of replication from the yeast $2\mu$ plasmid, and the LEU2 gene for selection in yeast cells. The strain is an adenine auxotroph, i.e., requires adenine for growth. Other adenine auxotrophs of yeast are typically used as recombinant hosts for heterologous protein expression, for example strains bearing mutations at the ADE 1 or ADE 2 loci. See, e.g., Kniskem, P. et al. in *Expression Systems for Processes for Recombinant DNA Products* (Hatch et al., eds.) ACS Symposium Series No.447 (ch.6) pp.65–75 (1991), and Schultz, L. et al. *Gene* 61, 123 (1987).

It would be desirable to identify the component(s) of complex media that affect fermentation performance, especially yields. Advantages of such discoveries would include a more reproducible fermentation process and a more predictable purification process.

Yeast extracts are commonly used in the media for yeast fermentations as the source for vitamins, trace elements and nitrogen nutrient. In many fermentation processes the nutrient which becomes limiting during the course of fermentation is the carbon source. The lot-to-lot variation of yeast extract due to variations in vendor's manufacturing processes dramatically affect recombinant yeast fermentation productivity and consistency, e.g. Recombivax HB® (a trademark of Merck & Co., Inc.) fermentation. The problem was partially solved in the past by the "brute-force" fermentation screening ("use-test") of new yeast extract lots. As a result, additional manpower and facilities had to be tied up, and sometimes "good" lots could not be secured due to delay in decision while other times "poor" lots were purchased and had to be thrown away. This disadvantage can be overcome by first identifying the critical and varying components in yeast extract that affect Recombivax HB® fermentation, and establishing rapid assay methods for these components. After a sufficiently representative database is built, the analytical results can be used to evaluate whether a particular yeast extract lot is desirable for Recombivax HB® fermentation.

The invention relates to a method to rapidly determine whether a yeast extract lot will be "good" for recombinant yeast fermentations, including that which produces HBsAg (Recombivax HB®), by measuring the contents of critical varying components such as adenine, trehalose and lactic acid. This simple and rapid screening procedure eliminates lots with suboptimal levels of these components and allows in most cases (about 80% of lots) superior and consistent fermentation productivity. The method also enables the improvement of fermentation yield by rational supplementation of those components to "poor" yeast extract lots.

Applicants have identified adenine and two metabolizable carbon sources (trehalose and lactate) as critical components in yeast extract causing fermentation inconsistency. Adenine is required for growth while the slowly metabolized trehalose supplies energy after growth phase for recombinant gene expression in the synthesis of expression product. The rapidly utilized lactate exerts a positive effect indirectly by sparing more ethanol as the carbon source for product synthesis. These effects on growth and production are mutually-dependent. A relatively high level of carbon sources (trehalose plus lactate, >4 g/42 g) and a mid level of adenine (0.06~0.1 g/42 g) are necessary characteristics of a good yeast extract lot for yeast cultivation and crude HBsAg production.

SUMMARY OF THE INVENTION

A method for improving the culture medium useful for the cultivation of recombinant yeasts and the production of recombinant proteins is provided. The medium is particularly useful for the cultivation of recombinant strains of *Saccharomyces cerevisiae* which produce HBsAg.

BRIEF DESCRIPTION OF THE DRAWINGS

Not applicable.

DETAILED DESCRIPTION OF THE INVENTION

The present invention is related to a general fermentation process for the production of recombinant proteins by yeast cells. The process of the present invention is demonstrated with the production of HBsAg by batch fermentation of strains of *Saccharomyces cerevisiae* transformed with a plasmid comprising the gene for HBsAg. As will be appreciated by one of ordinary skill in the art, the process of the present invention has a more general application to cultivation of other strains of *S. cerevisiae* and the production of other recombinant products and is not limited to HBsAg.

In general, yeast batch fermentation in complex medium is either a growth-limited process or a carbon source-limited process, depending on the adenine and trehalose/lactate contents of the YE (yeast extract) lot used. The concentration of these critical components in YE can vary dramatically due to variations in vendors' manufacturing processes. These inconsistencies contribute to fluctuations in fermentation performance, e.g., the amount of HBsAg produced. The analytical tools for adenine, trehalose and lactate in YE have been developed. Adenine content determines biomass production while carbon source (trehalose plus lactate) content affects antigen (HBsAg) product synthesis, and these two effects are related to each other. A mid-level adenine (0.06~0.1 g/42 g YE) and a high level trehalose plus lactate (>4 g/42 g YE) are the necessary requirements for a good lot, provided that the concentration of lactate does not exceed about 4.0 g/42 g YE. Concentrations of lactate exceeding about 4.0 g/42 g YE will cause significant change in fermentation pH profile. Many poor lots are improved by rational supplementation of adenine or trehalose or lactate or their combination.

In this invention, there is provided a method for improving culture medium with limiting carbon source for a recombinant yeast prototroph, comprising the steps of:
 a) providing a quantity of a given lot of yeast extract to be tested;
 b) measuring the concentrations of trehalose and lactate;
 c) adjusting the concentration of trehalose plus lactate to more than or equal to about 4.0 g/42 g of yeast extract, provided that the concentration of lactate is less than or equal to about 4.0 g/42 g yeast extract.

In one embodiment of this invention, there is provided a method for improving culture medium with limiting carbon source for a recombinant yeast prototroph, comprising the steps of:
 a) providing a quantity of a given lot of yeast extract to be tested;
 b) measuring the concentrations of trehalose and lactate;
 c) adjusting the concentration of trehalose plus lactate to between about 5.0 g/42 g of yeast extract and about 8.0 g/42 g of yeast extract, provided that the concentration of lactate is less than or equal to about 4.0 g/42 g yeast extract.

This invention also provides a method of identifying bad lots of yeast extract for fermentation with limiting carbon source for a recombinant yeast prototroph, comprising the steps of
 a) providing a quantity of a given lot of yeast extract to be tested;
 b) measuring the concentrations of trehalose and lactate; and
 c) identifying bad lots as those lots with suboptimal concentrations of trehalose or lactate.

In another embodiment of this invention, there is provided a method for improving culture medium with limiting carbon source for recombinant yeast adenine auxotrophs, comprising the steps of:
 a) providing a quantity of a given lot of yeast extract to be tested;
 b) measuring the concentration of one or more of adenine, trehalose and lactate;
 c) adjusting the concentrations of adenine to between about 0.06 to about 0.10 g/42 g of yeast extract, and of trehalose plus lactate to more than or equal to about 4.0 g/42 g of yeast extract, provided that the concentration of lactate is less than or equal to about 4.0 g/42 g yeast extract.

In another embodiment of this invention, there is provided a method for improving culture medium with limiting carbon source for recombinant yeast adenine auxotrophs, comprising the steps of:
 a) providing a quantity of a given lot of yeast extract to be tested;
 b) measuring the concentration of one or more of adenine, trehalose and lactate;
 c) adjusting the concentrations of adenine to between about 0.06 to about 0.10 g/42 g of yeast extract, and of trehalose plus lactate to between about 5.0 g/42 g of yeast extract and about 8.0 g/42 g of yeast extract, provided that the concentration of lactate is less than or equal to about 4.0 g/42 g yeast extract.

Another embodiment of this invention provides a method of identifying bad lots of yeast extract for recombinant yeast adenine auxotroph fermentation with limiting carbon source, comprising the steps of
 a) providing a quantity of a given lot of yeast extract to be tested;
 b) measuring the concentration of one or more of adenine, trehalose and lactate; and
 c) identifying bad lots as those lots with suboptimal concentrations of adenine, trehalose or lactate, or combination thereof.

Another embodiment of this invention is a method for improving culture medium with limiting carbon source for recombinant yeast adenine auxotrophs for the synthesis of recombinant Hepatitis B surface antigen, comprising the steps of:
 a) providing a quantity of a given lot of yeast extract to be tested;
 b) measuring the concentration of one or more of adenine, trehalose and lactate;
 c) adjusting the concentrations of adenine to between about 0.06 to about 0.1 g/42 g of yeast extract, and of trehalose plus lactate to more than or equal to about 4.0 g/42 g of yeast extract, provided that the concentration of lactate is less than or equal to about 4.0 g/42 g yeast extract.

Another embodiment of this invention is a method for improving culture medium with limiting carbon source for recombinant yeast adenine auxotrophs for the synthesis of recombinant Hepatitis B surface antigen, comprising the steps of:
 a) providing a quantity of a given lot of yeast extract to be tested;
 b) measuring the concentration of one or more of adenine, trehalose and lactate;
 c) adjusting the concentrations of adenine to between about 0.06 to about 0.1 g/42 g of yeast extract, and of trehalose plus lactate to between about 5.0 g/42 g of yeast extract and about 8.0 g/42 g of yeast extract, provided that the concentration of lactate is less than or equal to about 4.0 g/42 g yeast extract.

Another embodiment of this invention is a method of identifying bad lots of yeast extract for recombinant yeast adenine auxotroph fermentation with limiting carbon source in the synthesis of recombinant Hepatitis B surface antigen, comprising the steps of
  a) providing a quantity of a given lot of yeast extract to be tested;
  b) measuring the concentration of adenine, trehalose and lactate; and
  c) identifying bad lots as those lots with suboptimal concentrations of adenine, trehalose or lactate, or combination thereof.

It is understood that the yeast adenine auxotrophs are provided as illustrations of the techniques of identifying bad lots and rational supplementation of yeast extracts. Other yeast auxotrophs, as well as yeast prototrophs provide suitable sources for yeast extract analytical screening and supplementation for the purpose of synthesizing recombinant proteins.

In this invention, one preferred sum of the trehalose plus lactate content is more than or equal to about 4.0 g/42 g YE, provided that the concentration of lactate does not exceed about 4.0 g/42 g YE. This upper limit in lactate concentration avoids suboptimal yields from high fermentation pH. The concentration of trehalose is in principle unlimited, but at levels above about 8.0 g trehalose/42 g YE, it is typically not metabolized. At higher concentrations, no toxicity effect of trehalose has been observed. It is preferable to have at least both trehalose and lactate in the medium since they are providing an additional carbon source at different stages of fermentation. There are 42 g yeast extract (YE) per liter of the medium.

Improvement of Fermentation Performance of "Poor-Growth" Lots

It was observed that, in general, poor growth led to poor volumetric HBsAg (i.e. antigen) yield; yet abundant growth frequently also did not support good antigen production. Because the addition of $\geq 0.2$ g/L adenine boosted growth to the range of that obtained with a "super-growth, poor-yield" lot, it was possible that the ample biomass production might have depleted other nutrients/factors related to and necessary for antigen synthesis. Therefore an adenine titration study was carried out using a "poor-growth" lot, which supported low antigen titer as expected. The results showed that while the growth increased progressively as the adenine concentration increased (up to 0.2 g/L), there was apparently an optimal level of adenine for antigen yield. In this case, adding 0.1 g/L led to a 60% increase in titer. The on-line respiration profiles of the cultures growing in another yeast extract lot clearly demonstrated that the original medium was limited in adenine and the addition of 0.04 g/L of adenine boosted growth dramatically. A 40% increase in biomass and 20% increase in antigen titer were achieved compared to the control batch. The sharp drop of OUR (Oxygen Uptake Rate) at ~32 hrs suggests that the higher growth supported by the higher adenine concentration quickly depleted ethanol (accumulated from glucose fermentation by the culture), a known provider of energy source for antigen synthesis, resulting in a smaller increase in antigen titer than biomass.

Enzymatic Assay for Adenine in YE

A method based on Naher (Methods of Enzymatic Analysis 4, 1909 (1974)) was developed, in which adenine is deaminated by nitrous acid to hypoxanthine, and oxidized by xanthine oxidase rapidly and qunatitatively to xanthine and further to uric acid measurable at 293 nm (see Examples). The conversion of adenine to uric acid during the assay was complete and quantitative. Finally, no formation of uric acid was observed when xanthine oxidase was omitted.

The adenine content measured for a YE lot was found to be insensitive to heat-sterilization conditions, indicating that adenine/growth relationship established at the 2-L shake-flask scale is applicable to large scale.

Relationship Between YE Adenine Content and Fermentation Performance

The biomass and antigen production of lots at the 2-L scale was measured as they relate to adenine content. Good correlation was obtained between growth and adenine in that biomass increased with adenine until the measured content reached about 0.12 g/42 g yeast extract(YE): after that the adenine level was no longer the limiting factor for growth. But no direct relationship between adenine and antigen yield existed except that most "good-yield" lots ($\geq 38$ mg HBsAg/L) possessed a mid-level of adenine (0.06~0.10 g /42 g YE), although some "poor-yield" lots were also found in this range. Thus, a mid-range adenine content is a desirable but not sufficient condition for optimal antigen (HBsAg) production.

Identification of Trehalose and Lactate as Metabolizable Carbon Sources in YE

Supplementation of adenine to some YE lots boosted growth but decreased HBsAg specific production, and some "supergrowth" lots due to high adenine contents supported very poor antigen yields. The likely explanation was that the abundant growth depleted the energy source such as ethanol required for antigen synthesis. On the other hand, a similar amount of ethanol should be produced from glucose (which is constant in every fermentation), yet in many cases growth or YE adenine content alone could not predict antigen yield of the fermentation, and drastically different yields were obtained for lots with very similar adenine or biomass level. A carbohydrate HPLC analysis was employed to examine YE components in conjunction with fermentation kinetic analysis. It was discovered that there were two metabolizable components in essentially every YE lot, a major disaccharide peak and a smaller "lactate" peak, and their levels varied lot-to-lot. Since these two peaks decreased or disappeared after fermentation, the corresponding compounds must have contributed to the fermentation by serving as carbon/energy sources.

The disaccharide peak was assigned as trehalose, an isomer of maltose, because treating the YE sample with a specific trehalase resulted in reduction of this peak and the formation of a glucose peak. As for the "lactate" component, incubation of the YE sample with L-lactate 2-monooxygenase led to a decrease in the peak size and the formation of an acetate peak. In order to confirm the structures of these two components, their purification from YE was carried out by hot ethanol extraction followed by preparative HPLC on an analytical column. The purified compounds were identified as trehalose and lactate by NMR studies.

Trehalose (α-D-glucopyranosyl α-D-glucopyanoside) is a storage material synthesized by baker's yeast in response to environmental stress. Trehalose content amounts up to 20% on dry cell weight basis. Since vendors' cultivation and downstream processes could not be absolutely consistent, trehalose content in various YE lots was found by HPLC to range widely from <1 to >7 g/42 g YE. As for the lactate component, since baker's yeast does not accumulate this metabolite, the minor amount detected (mostly <3 g/42 g YE) is often present due to lactobacillus contamination during the vendors'manufacturing processes, a common phenomenon in the baker's yeast industry.

The utilization of trehalose and lactate from YE during a yeast fermentation at the 23-L scale was monitored. It was found that lactate was rapidly metabolized as carbon source for growth after glucose utilization, which delayed the depletion of the accumulated ethanol, a known energy source for antigen production. Broth pH increased during lactate utilization and dropped back down thereafter. Glycerol was accumulated but not re-utilized due to membrane impermeability. Trehalose was catabolized slowly during and after the oxidation of the accumulated ethanol, thus serving as carbon/energy source for the later phase of the fermentation during which recombinant product antigen (HBsAg) was being synthesized. Besides being an energy source, another plausible function of trehalose is the stabilization of cell membrane structure against environmental stress.

Relationship Between the Level of Trehalose Plus Lactate and Fermentation Performance Various lots which had been evaluated in 2-L yeast fermentations were analyzed for their trehalose and lactate contents. The relationship between carbon source (trehalose plus lactate) contents and biomass gave no apparent correlation to relate growth and YE carbon source content, as most fermentations were limited by adenine. But there is a readily apparent trend that up to 6 g/42 g YE higher carbon source content supported higher antigen titers. The majority of the "good" lots (yielding >38 mg HBsAg/L) had >4 g/42 g YE in carbon source and lots with less than this level were essentially all "poor". However, not all the lots with respectable carbon source contents were "good". About 80% of the "good" lots possess mid-level adenine (0.06~0.1 g/42 g YE).

Effect of Lactate Supplementation on Fermentation Performance

There was a positive effect of lactate supplementation at 23-L scale to a YE lot containing high adenine (0.13 g/L) and low carbon sources (2.7 g tre, 0.6 g lact/L). Since lactate metabolism was found to increase pH, the pH was manually controlled to match the control. Clearly, the presence of 4.5 g/L more lactate provided carbon source for growth, thus sparing the ethanol. The resulting delay of ethanol depletion (as reflected by $CO_2$ Evolution Rate or CER) made more energy source available for antigen synthesis and hence led to higher HBsAg titer.

New Mechanism of Trehalose Effect and Improvement of Poor Lots by Rational Supplementation One known function of trehalose is the protection of microbial membrane integrity against environmental stresses because of its unique characteristics in forming bonds with phosphodiester linkages in phospholipids. In the yeast fermentation, however, the positive effect of trehalose was often observed when trehalose was not intact, i.e., when it was split into glucose and catabolized. It appeared that trehalose affected yeast fermentation through slowly supplying glucose for growth and product synthesis. The later effect was major in that after ethanol depletion at 24~36 hrs (depending on the lot) which led to the cessation of exponential growth, trehalose became the sole carbon/energy source available for antigen synthesis, as the glycerol produced from glucose could not be re-utilized, and the lactate brought in by YE and Hy-soy had been depleted in earlier phase.

Based on such a new mechanism, a poor YE lot (high adenine, and low trehalose plus lactate content) is improved by providing additional trehalose. In one example, it was seen from the control that without additional trehalose, antigen synthesis essentially stopped when ethanol had depleted (judged by OUR) and most of the original trehalose was consumed at ~30 hrs. Addition of more glucose at 0 hr resulted in accumulation of more ethanol (and more non-usable glycerol) for growth, which slightly delayed the depletion of ethanol, and thus could only slightly increase antigen titer. When trehalose was supplemented to the level of about 8 g/42 g YE, similar catabolic profiles were observed, and trehalose utilization provided carbon/energy during synthesis phase which led to more active cells (as reflected by OUR profiles) and significantly higher antigen yield. It is noteworthy that more trehalose did not delay ethanol depletion as seen with more glucose, indicating different mechanisms and the importance of the slowly-released carbon/energy source which ensured the availability of energy for antigen synthesis.

The effect of trehalose supplementation to various low-to mid-trehalose lots at 23-L fermentor scale indicated that most of them were improved mainly through the increase in specific production, while the biomass was increased only slightly compared to antigen titer. In most cases the on-line OUR profiles showed the distinctive higher respiratory activities at the synthesis phase compared to the respective controls.

EXAMPLE 1

Culture Inoculum Development and Production Fermentation

The culture source for all the experiments was frozen seed stocks, generated from frozen vials of *Saccharamyces cerevisiae* 2150-2–3 (pHBS56-GAP347/33).

The medium for all seed stages was 5×Leu⁻ containing 90 g/L dextrose. The production fermentation medium was Enhanced YEHD, comprised of 42 g/L yeast extract (YE), 35 g/L Hy-Soy peptone and 17 g/L dextrose (sterilized separately), with the presterilization pH adjusted to 5.0. Polyalkylene glycol was added as antifoam at 0.5 ml/L for shake-flask fermentation and 1 ml/L for stirred-tank fermentation. Adenine, lactate or trehalose was added prior to sterilization, at the concentrations specified.

A frozen cell suspension (1.5 ml) was thawed at room temperature and inoculated to a 250-mL Erlenmeyer flask containing 50 ml of medium. After 24 h incubation on a rotary shaker (220 rpm. 28° C.), twenty ml of the culture were transferred to a 2-L Erlenmeyer flask containing 500 ml of medium, and cultivated for 24 -h on a rotary shaker at 180 rpm and 28° C. The culture was used as the inoculum for fermentation studies in the 2-L shake-flasks and in some 23-L tanks. For other 23-L scale fermentations, a third seed stage was included which was developed for 24 h in a 23-L tank containing 15 liters of medium, at 28° C. with an agitation of 600 rpm and aeration of 6 L/min.

For fermentation studies carried out at shake-flask scale, the 2-L baffled flask containing 200 ml of Enhanced YEHD medium was used. The flasks were inoculated with 4% (v/v) seed culture and incubated at 28° C. and 180 rpm on a rotary shaker for two days. For 23-L stirred-tank fermentations, an inoculum of 5% from the shake flask seed or 8% from the third stage seed was used. The tanks were operated at 28° C. with an agitation of 600 rpm, an aeration of 12 L/min, and a back pressure of 0.6 bar. Respiratory activities (Oxygen Uptake Rate or OUR, and $CO_2$ Evolution Rate or CER), dissolved oxygen and pH were monitored on-line, while carbohydrates were monitored off line by HPLC.

EXAMPLE 2

Analysis

Growth was measured by optical density (OD) at 660 nm on a spectrophotometer, or by dry cell weight (DCW). These two methods gave essentially the same conclusions. Carbon source compounds such as glucose, trehalose, lactate and ethanol were analyzed by HPLC system. To profile antigen production, cell pellets of 50 OD units were prepared from fermentation broth samples taken at various time points, washed once with PBS buffer and stored at −70° C. till breakage. The lysate was prepared by vortexing the cells with glass beads. The protein content in cell lysates was analyzed by the bicinchoninic acid method, and the HBsAg concentration was determined by enzyme immunoassay (EIA) using the commercially available assay kit. All results were back-calculated and expressed as fermentation titers (mg/L).

The data was based on the assays carried out at the same time and under the same conditions for the experimentals and the respective controls to minimize variations from assay kits, standards, and assay conditions. Similarly, all the comparisons were based on the same experiment to eliminate differences due to culture conditions. When two or more measurements were carried out, average results were used.

EXAMPLE 3
Measurement of Adenine Content in Yeast Extracts

Adenine content in various YE lots was determined by an enzymatic assay developed based on Naher (Methods of Enzymatic Analysis 4, 1909 (1974)) which involves adenine deamination by nitrous acid and oxidation by xanthine oxidase to give uric acid measurable at 293 nm. The procedure is as follows:
1. Prepare 42 g/L YE sample by adding 24.5 ml of water and 0.2 ml of 2 N HCl to 1.05 g YE powder and mixing throughly to get clear solution (the lot giving turbid solution is not desirable). Also prepare adenine standard solutions (0, 0.025, 0.05, 0.10, 0.20, 0.40 g/L) by diluting with water a 1.0 g/L, pH 2 stock solution (stable at 4° C. for months).
2. Mix throughly by vortexing 2.0 ml of the YE sample or the adenine standard with 0.9 ml of 20% (w/v) sodium nitrate and 0.1 ml of undiluted sulfuric acid in a 50-mL uncapped tube. Immediately put the mixture into a 37° C. water bath to incubate for 60 min with paper towel covering the uncapped tube.
3. After taking out the tube add 1.0 ml of 20% (w/v) sodium hydroxide solution and mix well to stop reaction. This mixture serves as the assay solution in the following steps and is found stable at 4° C. for at least a month.
4. Saturate Tris buffer (0.1 M, pH 8.0) with oxygen by sparging air to the buffer. Add 3.0 ml of this buffer and 30 $\mu$l of the assay solution to a 5-mL cuvette. Seal the cuvette with parafilm and invert to mix the content, and immediately read the extinction (E1) at 293 nm on a spectrophotometer blanked with the standard containing 0 g/L adenine. Two readings should be made for each measurement and the values should not differ more than 0.002.
5. Add 10$\mu$l of 1:10-diluted xanthine oxidase suspension (15.61 U/ml, diluted with 3.2 M ammonium sulfate) to the cuvette and seal the cuvette with parafilm. Invert to mix the content, and read the extinction at 292 nm the same way as above on the same spectrophotometer immediately and then every 5 min until a constant/maximal value (E2) is reached (generally in less than 30 min).
6. Adenine concentration in a YE lot (g/42 g YE) is estimated from its E value based on a standard curve generated from the authentic adenine samples (0, 0.025, 0.05, 0.10, 0.20, 0.40 g/L, treated the same way and at the same time as the YE samples). E is calculated according to the following equation ("blank" has 0 g/L of adenine):

$$E=(E2-E1)\text{sample} -(E2-E1)\text{blank}$$

EXAMPLE 4
Measurement of Trehalose and Lactate

Trehalose and lactate contents in various yeast extract (YE) lots were determined by HPLC method using an ion-exchange column. The procedure is as follows:
1. Prepare 42 g/L YE sample the same way as that for adenine analysis. Dilute the sample (1:5) with 0.005 M sulfuric acid (mobile phase) before filtering through a 0.45$\mu$ membrane. Also prepare trehalose (as dihydrate) standard solutions (0~2.0 g/L) and Na-lactate standard solutions (0~1.0 g/L) with the mobile phase.
2. Generate the standard curves for trehalose and lactate on an HPLC system, and then analyze the YE sample. The equipment includes a solvent delivery pump, an automatic sampler injector and a detector. A 20-$\mu$l sample is injected into column containing a polystyrene divinylbenzene cation exchange resin (for organic acids and alcohols) maintained at 60° C. The sample is eluted isocratically with 0.005 M sulfuric acid at 0.7 ml/min, and monitored for refractive index (RI) change. Sample peaks are identified and quantified by comparing with those of authentic compounds. Under these conditions, trehalose eluted at ~7.3 min and lactate at ~12.6 min.

EXAMPLE 5
Purification of Trehalose and Lactate

Purification of trehalose and lactate from YE in order to confirm the structures by NMR was achieved through hot ethanol extraction followed by preparative HPLC on an analytical column. To 50 g of YE was added 200 ml of ethanol and the mixture was stirred for 30 min in an 85~90° C. water bath. The filtrate was allowed to cool at room temperature and the resulted precipitate was collected. After washing with cold ethanol and dried with air, the precipitate was dissolved in 2 ml of water. The preparation, estimated to be ≧30% in weight purity in terms of trehalose, was injected and eluted repeatedly on the above analytical HPLC system for further purification (no prep column was available). The pooled trehalose and lactate fractions were dried by lyophilization before NMR structure determination.

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed:
1. A method of producing a yeast extract composition for use as an additive to culture media having a limiting carbon source concentration for a recombinant *Saccharomyces cerevisiae* prototroph, comprising the steps of:
   a) providing a quantity of yeast extract to be tested;
   b) measuring the concentrations of trehalose and lactate in said quantity of yeast extract;
   c) adjusting the concentration of trehalose plus lactate to more than or equal to 4.0 g per 42 g dry weight of yeast extract if the concentration of trehalose plus lactate in the yeast extract as measured in step b) is less than 4.0 g per 42 g dry weight of yeast extract;
   to produce a yeast extract composition for use as an additive to culture media having a limiting carbon source concentration for a recombinant *Saccharomyces cerevisiae* prototroph, wherein the yeast extract composition obtained has a concentration of trehalose plus lactate of more than or equal to 4.0 g per 42 g dry weight of yeast extract.
2. The method according to claim 1, wherein the adjustment in the concentration of trehalose plus lactate according to step c) is between about 5.0 g/42 g and about 8.0 g/42 g.

3. A method of producing a yeast extract composition for use as an additive to culture media having a limiting carbon source concentration for a recombinant *Saccharomyces cerevisiae* adenine auxotrophs, comprising the steps of:

a) providing a quantity of yeast extract to be tested;

b) measuring the concentrations of adenine, trehalose and lactate in said quantity of yeast extract;

c) adjusting the concentrations of adenine to between about 0.06/42 g to about 0.10 g/42 g dry weight of yeast extract if the concentration of adenine measured in step b) is less than 0.06 g/42 g dry weight, and adjusting the concentration of trehalose plus lactate to more than or equal to about 4.0 g/42 g dry weight of yeast extract if the concentration of trehalose plus lactate measured in step b) is less than 4.0 g/42 g dry weight, to produce, a yeast extract composition having a concentration of adenine between about 0.06/42 g to about 0.10 g/42 g dry weight of yeast extract, a concentration of trehalose plus lactate of more than or equal to 4.0 g per 42 g dry weight of yeast extract and a concentration of lactate of less than or equal to about 4.0 g/42 g dry weight of yeast extract.

4. The method according to claim 3, wherein the adjustment in the concentration of trehalose plus lactate according to step c) is between about 5.0 g/42 g and about 8.0 g/42 g.

5. A method of producing a yeast extract composition for use as an additive to culture media with limiting carbon source concentration for recombinant *Saccharomyces cerevisiae* adenine auxotrophs for the synthesis of recombinant Hepatitis B surface antigen, comprising the steps of;

a) providing a quantity of yeast extract to be tested;

b) measuring the concentrations of adenine, trehalose and lactate in said quantity of yeast extract;

c) adjusting the concentrations of adenine to between about 0.06/42 g to about 0.10 g/42 g dry weight of yeast extract if the concentration of adenine measured in step b) is less than 0.06 g/42 g dry weight, and adjusting the concentration of trehalose plus lactate to more than or equal to about 4.0 g/42 g dry weight of yeast extract if the concentration of trehalose plus lactate measured in step b) is less than 4.0 g/42 g dry weight, to produce a yeast extract composition having a concentration of adenine between about 0.06/42 g to about 0.10 g/42 g dry weight of yeast extract, a concentration of trehalose plus lactate of more than or equal to 4.0 g per 42 g dry weight of yeast extract and a concentration of lactate of less than or equal to about 4.0 g/42 g dry weight of yeast extract.

6. The method according to claim 5, wherein the adjustment in the concentration of trehalose plus lactate according to step c) is between about 5.0 g/42 g and about 8.0 g/42 g.

* * * * *